US008568758B2

(12) United States Patent  (10) Patent No.: US 8,568,758 B2
Daniels  (45) Date of Patent: Oct. 29, 2013

(54) CORN STEEP LIQUOR AS A BIOSTIMULANT COMPOSITION

(75) Inventor: Ralph S. Daniels, East Greenwich, RI (US)

(73) Assignee: Daniels AgroSciences, LLC, East Greenwich, RI (US)

( * ) Notice: Subject to any disclaimer, the term of this patent is extended or adjusted under 35 U.S.C. 154(b) by 384 days.

(21) Appl. No.: 12/847,706

(22) Filed: Jul. 30, 2010

(65) Prior Publication Data

US 2012/0028801 A1  Feb. 2, 2012

(51) Int. Cl.
*A01N 25/32* (2006.01)

(52) U.S. Cl.
USPC .......... 424/406; 71/25; 424/93.462; 424/405; 424/725; 424/750

(58) Field of Classification Search
None
See application file for complete search history.

(56) References Cited

U.S. PATENT DOCUMENTS

| | | | |
|---|---|---|---|
| 4,075,361 A | 2/1978 | Oberg | |
| 7,052,725 B2 | 5/2006 | Chang et al. | |
| 2004/0043445 A1 | 3/2004 | Daniels | |
| 2007/0065540 A1* | 3/2007 | Jones et al. | 426/53 |
| 2007/0131010 A1 | 6/2007 | Binder et al. | |
| 2008/0113064 A1 | 5/2008 | Bevans et al. | |
| 2008/0134737 A1 | 6/2008 | Binder et al. | |
| 2009/0031775 A1 | 2/2009 | Bevans et al. | |
| 2011/0009262 A1 | 1/2011 | Soejima et al. | |

FOREIGN PATENT DOCUMENTS

| | | |
|---|---|---|
| JP | 04198080 A | 7/1992 |
| JP | 10338584 A | 12/1998 |
| JP | 2003335596 A | 11/2003 |
| WO | 02-10331 A2 | 2/2002 |
| WO | 2009104405 A1 | 8/2009 |
| WO | WO-2009118027 * | 10/2009 |
| WO | 2010083106 A1 | 7/2010 |

OTHER PUBLICATIONS

Fox, J.E., & Miller, C., "Factors in Corn Steep Water Promoting Growth of Plant Tissues", Plant Physiology, 1959, vol. 34, pp. 577-579.
International Search Report and Written Opinion issued Aug. 30, 2011 in related PCT Application No. PCT/US2010/058315.
Nakano, et al., "Effects of Organic Liquid Fertilizer (Corn Steep Liquor) on Initial Growth and Rhizosphere of Tomato Plant" Department of Protected Cultivation (NIVOT), Taketoyo, Aichi 470-2351, Japan; Graduate School of Bioagricultural Science, Nagoya University, Nayoga 464-8601, Japan, vol. 38, No. 4 Mar. 27, 2000.
Yoshida, Ryuji, "Effect of Water-Extract Prepared from Maize Immature Seeds on Growth and Yield in Vegetable Crops" Toyama Prefectural University, Kosugimachi, Toyama 939-03, The Crop Science Society of Japan, pp. 117-120, 1991.

* cited by examiner

*Primary Examiner* — Neil Levy

(57) ABSTRACT

Aspects of the invention relate to organic biostimulant compositions, including, for example, formulations comprising corn steep liquor (CSL) and water. In certain illustrative embodiments, the organic biostimulant composition further comprises from one to five microbial strains as an inoculant. Another aspect of the invention relates to a method of cultivating plants that comprises the steps of preparing an organic biostimulant composition comprising water and CSL, and applying the organic biostimulant composition through a delivery system to a growth medium supporting plants.

17 Claims, 2 Drawing Sheets

CORN STEEP LIQUOR AS A BIOSTIMULANT COMPOSITION

FIELD OF THE INVENTION

The present invention is directed toward organic biostimulant compositions and uses comprising corn steep liquor. The organic biostimulant composition may further comprise microbial inoculants.

BACKGROUND OF THE INVENTION

Plant growth is dictated by both internal and external factors. The internal mechanisms originate in the genetic makeup of the plant and influence the extent and timing of its growth. These internal mechanisms are regulated by signals of various types transmitted within the plant cells, between the cells, or all around the plant itself. The external factors are directly related to the immediate environment surrounding the plant. These external influences affect plant growth and include such factors as light, temperature, water, and nutrients. The external environment can place constraints on the extent to which internal mechanisms can permit the plant to grow and develop, with two of the most important factors being related to the availability of water and nutrient supplies in the soil. Cell expansion is directly related to water supply, and thus any deficit results in a smaller plant. Mineral nutrients are needed for the biochemical processes of the plant. When nutrients are in insufficient supply, growth will be less vigorous, or in extreme cases, it will cease altogether. The nutrients necessary for plant growth include: the primary macronutrients nitrogen (N), phosphorous (P), and potassium (K); the secondary macronutrients calcium (Ca), sulfur (S), and magnesium (Mg); and the micronutrients or trace minerals boron (B), chlorine (Cl), manganese (Mn), iron (Fe), zinc (Zn), copper (Cu), Molybdenum (Mo), and Selenium (Se). Optimal temperatures are also necessary for plant growth. The required temperature range will depend on the species, but most plants grow slowly at low temperatures, i.e., 0° C. to 10° C., and some tropical plants are damaged or even killed at low, but above-freezing temperatures. Light is also important in the control of plant growth, in that it drives the process of photosynthesis.

Corn steep liquor (CSL) is a liquid by-product of the corn wet-milling process used to obtain corn starch and high fructose corn syrup (HFCS). CSL consists of concentrated corn solubles extracted during a process whereby corn, after having been shelled and air-cleaned, is soaked in water (steeped), and then fractionated into its principal components by a combination of flotation and wet-screening procedures. During steeping, the soluble materials are dissolved, the corn is softened, and its structure weakened and broken, which facilitates the grinding and further separations of its components. The resulting concentrate is crude corn steep liquor, which may be further combined with gluten and fibrous materials to be sold as animal feed, or it can be used for other purposes, with or without further processing. Besides being used as a nutrient for ruminant animals, CSL has also been used in the penicillin industry as a culture medium for penicillin production.

CSL (CAS No. 66071-94-1) is commercially available as approximately 50% water with the rest made up of corn components; water soluble proteins, free amino acids, minerals, vitamins, reducing sugars (e.g., dextrose), and other natural organic acids (e.g., lactic acid). CSL is a viscous slurry with a color ranging from light to dark brown. CSL has a pH of about 4.0 and consists predominantly of naturally occurring nutritive materials such as water soluble proteins, amino acids (e.g., alanine, arginine, aspartic acid, cysteine, glutamic acid, histidine, isoleucine, leucine, lysine, methionine, phenylalanine, proline, threonine, tyrosine, valine), vitamins (e.g., B-complex), carbohydrates, organic acids (e.g., lactic acid), minerals (e.g., Mg, P, K, Ca, S), enzymes and other nutrients. This CSL is the starting material used in the compositions of the present invention.

Biostimulants are compounds that produce non-nutritional plant growth responses and reduce stress by enhancing stress tolerance. This is in contrast to fertilizers, which produce a nutritional response. Many important benefits of biostimulants are based on their ability to influence hormonal activity. Hormones in plants (phytohormones) are chemical messengers regulating normal plant development as well as responses to the environment. Root and shoot growth, as well as other growth responses are regulated by phytohormones. Compounds in biostimulants can alter the hormonal status of a plant and exert large influences over its growth and health. Sea kelp, humic acids and B Vitamins are common components of biostimulants that are important sources of compounds that influence plant growth and hormonal activity. Antioxidants are another group of plant chemicals that are important in regulating the plants response to environmental and chemical stress (drought, heat, UV light and herbicides). When plants come under stress, "free radicals" or reactive oxygen molecules (e.g., hydrogen peroxide) damage the plants cells. Antioxidants suppress free radical toxicity. Plants with the high levels of antioxidants produce better root and shoot growth, maintain higher leaf-moisture content and lower disease incidence in both normal and stressful environments. Applying a biostimulant enhances antioxidant activity, which increases the plant's defensive system. Vitamin C, Vitamin E, and amino acids such as glycine are antioxidants contained in biostimulants.

The rhizosphere is the region of soil that is immediately adjacent to and affected by plant roots. The rhizosphere is an environment whereby plants, soil, microorganisms, nutrients and water meet and interact. Bacteria present in the rhizosphere feed on shed plant cells as well as proteins and sugars released by plant roots. The interaction between various root microorganisms can play a part in increasing nutrient uptake by plants in nutrient poor environments. Exemplary interactions include symbiotic (e.g., mycorrhizal) and other specific (e.g., nitrogen fixing) associations.

Microbial inoculants are agricultural amendments that use beneficial microbes (e.g., bacteria or fungi) to promote plant health. When added to seeds and soils, microbial inoculants have proven beneficial for use in field crops. Many of the microbes involved form symbiotic relationships with the target crops. While microbial inoculants are applied to improve plant nutrition, they can also be used to promote plant growth by stimulating plant hormone production. Microbial inoculants may also be used to initiate systemic acquired resistance (SAR) of crop species to several common crop diseases. Typical genera of bacterial microorganisms include, for example, *Azospirillum, Rhizobium, Bacillus, Pseudomonas, Streptomyces*, and *Zooglia*. *Rhizobium* is a genus of nitrogen-fixing soil bacteria that form symbiotic associations within nodules on the roots of legumes. This increases nitrogen nutrition and is important to the cultivation of soybeans, chickpeas and many other leguminous crops. For non-leguminous crops, *Azospirillum* has been demonstrated to be beneficial for nitrogen fixation and plant nutrition. *Bacillus, Pseudomonas*, and *Streptomyces* bacteria provide some, if not all, the following benefits: increased plant growth, decomposition of organic matter and pesticide residues, increased nutrient cycling and nitrogen fixation, increased resistance to environmental extremes, increased solubility of minerals for plant uptake, increased production of natural plant growth hormones, improved soil structure, and enhanced seed germination and viability. To improve phosphorous nutrition, the use of phosphate-solubilising bacteria (PSB) such as *Agrobacterium radiobacter* has also received attention, acting to break down inorganic soil phosphates to simpler forms that enable uptake by plants. Microbial inoculants may also comprise fungi. Several different fungal inoculants have been used to benefit plant health, including the genus *Trichoderma* and strains such as *Arbuscular mycorrhiza* and *Piriformis indica*. *Trichoderma* provides many of the same benefits to plant health as the aforementioned bacteria, including increasing the plant's resistance to environmental extremes and producing natural plant growth hormones.

Typically, a microbial inoculant contains a "cocktail" of multiple strains of microorganisms, i.e., 40 or more. By inoculating with multiple strains of microorganisms, the underlying problem of not knowing which individual microbe is responsible for the desired plant characteristic or response does not have to be addressed. Presently, microbiologists do not thoroughly understand the individual growth and survival characteristics of each particular beneficial microorganism, including their nutritional and environmental requirements. In addition, there is a general lack of understanding as to the ecological relationships and interactions between the microorganisms themselves. Another prevailing theory is that "singular" (i.e., less than five strains) microbial inoculation is often times not of a sufficient inoculum density to grow, survive and adapt in the soil environment. Therefore, "singular" microbial inoculants are not commonly used in soil or plant amendment products such as biostimulant compositions, plant foods or fertilizers.

Soil bacteria are able to perform a variety of services, including degradation of organic matter, disease suppression, and nutrient transformations inside roots. In general, they are responsible for transforming inorganic constituents from one chemical form to another. The majority of the beneficial soil-dwelling bacteria need oxygen (aerobic), while those that do not require air are referred to as anaerobic. Important soil bacteria include nitrogen-fixing bacteria, nitrifying bacteria, denitrifying bacteria and actinomycetes.

Biostimulants may act to stimulate the growth of microorganisms that are present in soil or other plant growing medium. Prior studies have shown that when biostimulants comprising specific organic seed extracts (e.g., soybean) were used in combination with a microbial inoculant, the biostimulants did not enhance the rhizosphere population of native microbes, but were capable of stimulating growth of microbes included in the microbial inoculant. Thus, it is desirable to obtain a biostimulant, that, when used with a microbial inoculant, is capable of enhancing the population of both native microbes and inoculant microbes.

OBJECTS OF THE INVENTION

It is an object of the present invention to provide an organic biostimulant composition comprising CSL. It is an object of at least certain embodiments of the invention (that is, not necessarily all embodiments of the invention) to provide organic biostimulant compositions that optimize plant growth and production. It is an object of at least certain (but not necessarily all) embodiments of the invention to provide organic biostimulant compositions having improved formulations. It is an object of at least certain embodiments of the invention (but not necessarily all) to provide a method for cultivating plants with organic biostimulant compositions that optimize plant growth and production. These and other objects, features and advantages of the invention or of certain embodiments of the invention will be apparent to those skilled in the art from the following disclosure and description of exemplary embodiments.

SUMMARY OF THE INVENTION

The following presents a simplified summary of aspects of the inventive products, compositions, and methods disclosed here. This summary is not an extensive overview, and it is not intended to identify all or only key or critical elements or to delineate the scope of the inventive products, compositions and methods covered by the claims. The following summary merely presents some concepts and aspects of the disclosure in a simplified form as a prelude to the more detailed description provided below of certain exemplary and non-limiting embodiments of the invention.

Aspects of the embodiments disclosed here are directed toward organic biostimulant compositions comprising water and corn steep liquor. In certain exemplary embodiments, the concentration of corn steep liquor in the biostimulant composition is between about 0.10% and 100% by weight. When used at 100% by weight, the CSL composition still includes water, since the commercial CSL starting material exists as a 50% water-based composition. As used herein, the CSL starting material is viewed as a single product, to which additional water and/or other materials are added if desired. For example, the organic biostimulant composition may further comprise a supplement selected from the group comprising natural glycerol, humate, fulvate, acetic acid, propionic acid, citric acid, lactic acid, or combinations thereof. In certain embodiments, the organic biostimulant is effective in enhancing the growth of indigenous microorganisms in a growth medium.

Further aspects of the embodiments disclosed here are directed toward organic biostimulant compositions comprising water, corn steep liquor and from one to five microbial strains as an inoculant. In certain exemplary embodiments the number of microbial strains in the inoculant is from one to three. In certain exemplary embodiments at least one microbial strain is *Bacillus subtilis*. In certain exemplary embodiments the organic biostimulant is effective in enhancing the growth of indigenous microorganisms in a growth medium and the one to five microbial strains in the inoculant.

Further aspects of the embodiments disclosed here are directed toward a method of cultivating plants, comprising the steps of: (a) preparing an organic biostimulant composition comprising water and corn steep liquor; and (b) applying the organic biostimulant composition through a delivery system to a growth medium supporting plants. The organic biostimulant composition may further comprise from one to five microbial strains as an inoculant. In certain embodiments, the growth medium is deficient in nutrients and microbes.

BRIEF DESCRIPTION OF THE DRAWINGS

A more complete understanding of the present disclosure and the advantages thereof may be acquired by referring to the following description in consideration of the accompanying drawings, wherein.

DETAILED DESCRIPTION OF THE INVENTION

Figure 1:
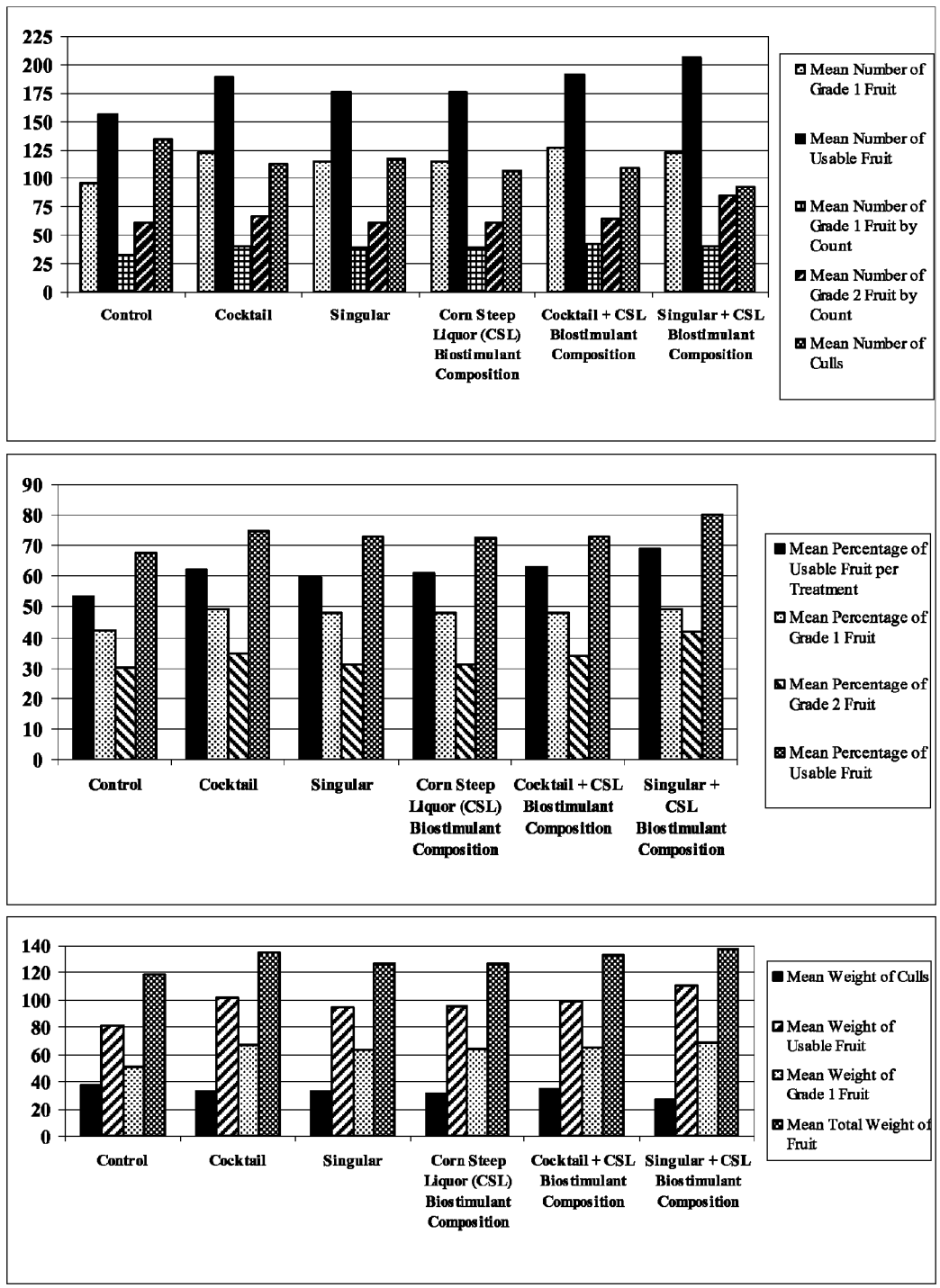
FIG. 1 is a representation of various results from field testing performed on tomato plants using different treatments with agricultural amendments, including treatments comprising CSL.

In the following description of the various embodiments, reference is made to the accompanying drawings, which form a part hereof, and in which is shown by way of illustration, various embodiments in which one or more aspects of the disclosure may be practiced. For convenience, the various embodiments discussed below are uses, methods and compositions for organic biostimulant compositions. It is to be understood that other embodiments may be utilized, and chemical, physical and functional modifications may be made without departing from the scope of the present disclosure.

By way of introduction, aspects of the disclosure provide an organic biostimulant composition comprising corn steep liquor (CSL) and a diluent, e.g., water. Field tests conducted in accordance with this disclosure (and described in detail below) reveal that organic biostimulant compositions comprising CSL yield superior results over those currently offered in the commercial marketplace.

As used here, the term "fertilizer" refers to a material or combination of materials which when added to soil, improves the rate of growth or health of plants, and/or increases the yield of plant fruits. Fertilizer, also referred to here as plant food, supplements the soil with varying amounts of nutrients necessary for plant growth, and thus produces a nutritional response by the plant. Microorganisms in the soil decompose fertilizer to make the nutrients available for use by plants. Fertilizer may be organic or inorganic, and may be liquid or solid in form. The term "organic fertilizer" refers to a fertilizer produced by processing biological material, such as animal manures or plant materials, and is characterized by a slow release of nutrients to the surrounding environment. The term "inorganic fertilizer" refers to a fertilizer produced by processing mineral and/or synthetic material. Inorganic fertilizers typically contain the three primary nutrients (nitrogen, phosphorous, and potassium) and are characterized by their fast release capability. While inorganic fertilizers supply sufficient amounts of these three macronutrients, they typically do not contribute to the structure or texture of the growth medium or contribute toward the growth and reproduction of microbes found in the soil that are beneficial to plants. It is also well-known that when inorganic fertilizers are misapplied, they can burn both plant roots and foliage.

As used here, the term "biostimulant" refers to any substance that acts to stimulate the growth of microorganisms that may be present in soil or other plant growing medium. The level of microorganisms in the soil or growing medium is directly correlated to plant health. Microorganisms feed on biodegradable carbon sources, and therefore plant health is also correlated with the quantity of organic matter in the soil. While fertilizers provide nutrients to feed and grow plants, biostimulants provide biodegradable carbon, e.g., molasses, carbohydrates, e.g., sugars, to feed and grow microorganisms. Unless clearly stated otherwise, a biostimulant may be comprised of a single ingredient or a combination of several different ingredients, and the enhanced microbial activity may be attributed to one or more of the ingredients, either acting independently or in combination.

A "diluent" is defined herein as a substance which is non-reactive with the components of the CSL. Diluents may be aqueous or organic in nature. As described above, commercial CSL is produced as a 50% mixture with water, and biostimulant compositions can be formed by adding further volumes of diluent, e.g., water, to the concentrated CSL. In certain exemplary embodiments, CSL is present in the biostimulant composition at a concentration in the range of about 0.10% and 100% by weight; including for example, between about 0.10% and 10% by weight; further including between about 10% and 90% by weight; further including between about 20% and 80% by weight; further including between about 40% and 60% by weight. The concentration of CSL will depend to a degree upon the desired rate of application of the biostimulant composition, the targeted use, and the other components of the composition.

Water is a basic ingredient in the biostimulant compositions disclosed here; typically being the vehicle or liquid portion in which any remaining ingredients are dissolved, emulsified, suspended, or dispersed. Purified water can be used in the manufacture of certain embodiments of the biostimulant compositions disclosed here, and water of a standard biostimulant composition quality can be employed in order not to adversely affect the composition. The water typically will be clear, colorless, free from objectionable minerals, tastes, and odors, free from unwanted organic matter, low in alkalinity, and of acceptable microbiological quality based on industry and government standards applicable at the time of producing the biostimulant composition. In certain typical embodiments, water is present at a concentration of from about 0% and 99.9% by weight of the biostimulant composition, e.g., between about 90% and 99.9% by weight, e.g., between about 10% and 90% by weight, e.g., between about 20% and 80% by weight, e.g., between about 40% and 60% by weight. The concentration of water will depend to a degree upon the rate of application of the biostimulant composition, the targeted use, the other components of the composition, and other factors recognized by those skilled in the art.

In at least certain exemplary embodiments the water used in biostimulant compositions disclosed here is "treated water," which refers to water that has been treated to reduce the total dissolved solids of the water prior to optional supplementation, e.g., with calcium as disclosed in U.S. Pat. No. 7,052,725. Methods of producing treated water are known to those of ordinary skill in the art and include deionization, distillation, filtration, and reverse osmosis ("r-o"), among others. The terms "treated water", "purified water", "filtered water", "demineralized water", "distilled water" and "r-o water" are understood to be generally synonymous in this discussion, referring to water from which substantially all mineral content has been removed, typically containing no more than about 500 ppm total dissolved solids, e.g., 250 ppm total dissolved solids.

As used here, "microbial inoculant" refers to a substance comprising microorganisms, i.e., microbes, which are beneficial to plant health. The microbial inoculants may comprise specific strains of microorganisms, including live strains or those in spore form. Such microbial inoculants may comprise, but are not limited to, bacteria, e.g., including *Azospirillum, Rhizobium, Bacillus, Pseudomonas, Streptomyces, Zooglia, Agrobacterium radiobacter*, or combinations thereof; fungi, e.g., including *Arbuscular mycorrhiza, Piriformis indica*, or combinations thereof; protozoa; algae; viruses; or combinations thereof. Additional and alternative microorganisms will be recognized by those skilled in the art given the benefit of this disclosure.

In certain exemplary and non-limiting embodiments disclosed here, the biostimulant compositions comprise from one to five microbial strains as an inoculant, e.g., from one to four microbial strains, e.g., from one to three microbial strains, e.g., from one to two microbial strains. The number of microbial strains will depend to a degree upon the targeted use, the particular chosen strain(s), their interaction with each other and the other components of the composition, and other factors recognized by those skilled in the art.

In certain exemplary embodiments, the microbial inoculant comprises *Bacillus subtilis*, a rod-shaped, Gram-positive, catalase-positive bacterium commonly found in soil and decomposing plant residue. *B. subtilis* is capable of enduring harsh environmental conditions, such as high temperatures and has been found to contribute to nutrient cycling. This species has been widely used in industry for the production of enzymes and specialty chemicals.

In certain exemplary embodiments, the microbial strain(s) may be indigenous to the targeted soil or growth medium environment. As used here, "indigenous" refers to microbial strains that originate, grow, produce, live and occur naturally in a particular targeted soil or growth medium environment. There are many families and species of microorganisms in the soil, including *Pseudomonas, Bacillus, Nocardia, Flavobacterium, Micrococcus, Rhizobium, Trichoderma*, and various other bacteria, yeasts, fungi, and the like. In certain exemplary embodiments the inoculant comprises at least one indigenous microbial strain. In certain exemplary embodiments, the microbial strain(s) may be non-indigenous or present at a low concentration in the targeted soil or growth medium environment. As used here, "non-indigenous" refers to microbial strains that originate, grow, produce, live and occur beyond the natural range or natural zone of the targeted soil or growth medium environment. In certain exemplary embodiments the inoculant comprises at least one non-indigenous microbial strain. In certain exemplary embodiments the microorganisms may comprise a combination of microorganisms that are indigenous and non-indigenous to the targeted soil or growth medium environment.

Field tests conducted in accordance with this disclosure (and described in detail below) reveal that when CSL is used in a biostimulant composition or is used in combination with a microbial inoculant, the resulting biostimulant composition yielded superior results over other treatments. For example, results indicate that organic biostimulants comprising CSL enhance the growth of indigenous microorganisms (e.g., native soil bacteria) in a growth medium. In particular, the results indicate that microbial inoculants used in combination with CSL based biostimulants enhance the growth of both indigenous microorganisms (e.g., native soil bacteria) in a growth medium and inoculant microbes (e.g., inoculant strain *Bacillus subtilis*). This is an improvement over previous studies, where only the inoculant microorganisms exhibited enhanced growth and activity. In addition, the study also revealed that when biostimulant comprising CSL and a microbial inoculant comprising a "singular" (i.e., from one to five strains) microorganism, the composition yielded superior performance over compositions comprising a "cocktail" (i.e., 40 or more strains) of microorganisms. This was very surprising, given that, as previously explained, the prevailing theory is that the "cocktail" inoculant approach is superior to the "singular" approach.

The biostimulant compositions disclosed here may be manufactured, distributed, and/or stored in different physical states and/or forms, including, for example, as a dry or wet solid, an aqueous solution, a gel, or slurry. In certain embodiments, aqueous solutions may be introduced and/or removed to alter the state or form. Likewise, the microbial inoculant may take on any of a variety of forms, non-limiting examples include, a solid carrier, a paste, a gel, a liquid, an encapsulated form, a component in a growth medium, or combinations thereof. The biostimulant composition disclosed here may comprise one or more distinct compositions that are then used in combination in practice.

In certain exemplary and non-limiting embodiments disclosed here, the biostimulant compositions may comprise an oilseed extract as an additional biostimulant ingredient. Oilseed extract is obtained from the caustic refining of crude vegetable oils. Since refined vegetable oils are used in food products, e.g., cooking oils, shortenings and margarine, the crude oils obtained from their respective seeds must be purified to remove the undesirable constituents that would impair their commercial viability (e.g., shelf life, etc.). The refining byproduct lipid (RBL), or soapstock, as it is known in the trade, is split into oil and water components. When the acidic aqueous fraction is brought to approximate neutrality by use of a nutrient base the resultant liquid is oilseed extract. Analysis of oilseed extract shows it contains the three (3) primary plant nutrients: N, P, K; the three (3) secondary plant nutrients: S, Ca, and Mg; and most, if not all of the trace element micronutrients, such as Cu, Fe and Zn. In addition, oilseed extract contains high levels of soluble carbohydrates that encourage growth of beneficial microorganisms.

In certain exemplary and non-limiting embodiments disclosed here, the biostimulant compositions may comprise plant nutrients as an additional biostimulant ingredient. Non-limiting suitable examples are provided by Daniels Professional Plant Food®. In certain exemplary embodiments, the Daniels Professional Plant Food® is a complete liquid fertilizer; 10N: $4P_2O_5$: $3K_2O$ (10-4-3). Although not classified as an organic fertilizer, this product does contain sufficient biodegradable carbon to exhibit organic properties. The base is produced from soybean, corn germ and/or other oilseeds, and the process is similar to that of oilseed extraction, described above. For fertilizer production purposes, potassium hydroxide, rather than sodium hydroxide, is used for free fatty acid removal from the crude vegetable oil as well as germination compounds that have been extracted from seeds, i.e., seed Extract®. Additional inorganic nutrients are added to the aqueous phase obtained from splitting soapstock to comply with a determined analysis. Daniels Professional Plant Food® may be produced from any of a number of different oil seeds, non-limiting examples including sunflower, corn, rapeseed, sesame, safflower, peanut, palm, olive, cottonseed, coconut, flax, canola, or combinations thereof.

In certain exemplary and non-limiting embodiments disclosed here, the biostimulant compositions may further comprise Daniels Pinnacle® 3-1-1 Organic Professional Plant Food. This particular plant food combines soluble organic nitrogen and Chilean nitrate with oilseed extract. The Pinnacle® plant food is certified organic in the United States, but due to the use of nitrates, it has not been certified as organic in many foreign countries, including the European Union. A new organic fertilizer is disclosed in co-pending patent application Ser. No. 12/835,006, filed Jul. 12, 2010, the disclosure of which is hereby incorporated herein by reference.

In certain exemplary and non-limiting embodiments disclosed here, the biostimulant composition is organic. For a biostimulant composition to be organic it must satisfy specific governmental standards. The governmental standards may vary from country to country, and in fact the regulations for the European Union are slightly different from those of the United States. The term "organic" as used in the pending application is intended to represent that the fertilizer has satisfied the standards for being denoted as organic in both the United States and the European Union. The United States Department of Agriculture (USDA) regulates organic certification within the United States through a National Organic Program (NOP). To qualify to use the organic label the requesting organization must be certified as satisfying a variety of guidelines by an NOP accredited certification agency. One such requirement for certification is by abiding by a National List that is produced by NOP. The National List identifies what can and cannot be included in certified organic products. Specifically, all non-synthetic (natural) materials are allowed, unless specifically prohibited and synthetic substances and ingredients and nonagricultural substances are prohibited unless specifically allowed. Council Regulation (EC) No 834/2007 regulates organic production and labeling of organic products within the European Union (EU). To claim a product is organic, an organization must gain approval from a certification agency. Biostimulant compositions may only be used if they have been authorized for use in organic products and mineral nitrogen biostimulant products may not be used. One key distinction between the EU and the US is that the EU prohibits the use of sodium nitrate and all other nitrates in organic products. Therefore, for a biostimulant composition to be certified organic in both the US and the EU it may not have nitrates.

In certain exemplary and non-limiting embodiments disclosed here, the biostimulant compositions may comprise a supplement as an additional biostimulant ingredient. Such additional supplements may include, but are not limited to, glycerol, humates (humic acid), fulvates (fulvic acid), acetic acid, propionic acid, citric acid, lactic acid, or combinations thereof.

In certain exemplary and non-limiting embodiments disclosed here, the biostimulant compositions may comprise an extract as an additional biostimulant ingredient. Such additional extracts may include, but are not limited to, botanical extracts, fermented plant extracts, e.g., herbal teas, compost teas, or combinations thereof.

In certain exemplary and non-limiting embodiments disclosed here, the biostimulant compositions may comprise additional sources of nitrogen. Such additional sources of nitrogen may include, but are not limited to, protein supplements such as hemp protein powder, soy protein powder, or combinations thereof.

In certain exemplary and non-limiting embodiments disclosed here, the biostimulant compositions may comprise amino acids as an additional biostimulant ingredient. Amino acids may act as an energy source for increased plant metabolism and improve the plant's nutrient absorption. Such additional amino acids may include, but are not limited to, tryptophan, asparagine, glutamine, glycine, selenocysteine, serine, ornithine, taurine, or combinations thereof.

In certain exemplary and non-limiting embodiments disclosed here, the biostimulant compositions may comprise vitamins and/or minerals as an additional biostimulant ingredient. Vitamins may act as catalysts for beneficial enzymes and act to enhance plant metabolism. Folic acid and Biotin (two components of the Vitamin B complex) also act to enhance microbial and plant growth. Such vitamins and minerals may include, but are not limited to, Boron, Copper, Iron, Manganese, Zinc, Molybdenum, Chlorine, Phosphorous, Potassium, Calcium, Magnesium, Sulfur, or combinations thereof.

In certain exemplary and non-limiting embodiments disclosed here, the biostimulant compositions may comprise a carbohydrate as an additional biostimulant ingredient. Such carbohydrates may include, but are not limited to, glucose, galactose, fructose, arabinose, xylose, sucrose, lactose, maltose, amylase, amylopectin, glycogen, glyceraldehyde, ribose, or combinations thereof.

In certain exemplary and non-limiting embodiments disclosed here, the biostimulant compositions may comprise a natural sugar as an additional biostimulant ingredient. Natural sugars typically refer to sugars derived from plant material, and act as a source of energy and carbon for plants and microbes. Such natural sugars may include, but are not limited to, fructose, sucrose, glucose, lactose, maltose, or combinations thereof.

In certain exemplary and non-limiting embodiments disclosed here, the biostimulant compositions may comprise an organic acid as an additional biostimulant ingredient. Such organic acids may include, but are not limited to, lactic acid, acetic acid, propionic acid, citric acid, glucuronic acid, formic acid, humic acid, fulvic acid, or combinations thereof.

In certain exemplary and non-limiting embodiments disclosed here, the biostimulant compositions may comprise an enzyme as an additional biostimulant ingredient. Such enzymes may include, but are not limited to, photolyase, lipase, protease, lipase, amylase, cellulose, catalase, or combinations thereof.

In certain exemplary and non-limiting embodiments disclosed here, the biostimulant compositions may be formulated to be released over a certain period of time, i.e., time-released. Such compositions may be formulated to release over time periods comprising hours, days, weeks, or months.

In certain exemplary and non-limiting embodiments disclosed here, the biostimulant composition may also include an organic pesticide. The organic pesticide may be any suitable material, substance, organism or combination thereof compatible with the biostimulant composition and the microorganisms beneficial to plant growth.

In certain exemplary and non-limiting embodiments disclosed here, the biostimulant composition is effective in enhancing the growth of indigenous microorganisms in a growth medium. In certain exemplary and non-limiting embodiments disclosed here, the biostimulant composition is effective in enhancing the growth of indigenous microorganisms in a growth medium and microbial strains included as an inoculant. As used here, the term "effective in enhancing the growth" or "enhances the growth" means being capable of or producing an increase in population, an improvement in health, an improvement in reproductive capacity, an improvement in the rate of growth and/or population, any combination of these, or providing any other tangible benefit to a microorganism or combination of microorganisms.

In certain exemplary and non-limiting embodiments disclosed here, a method for cultivating plants is provided, comprising: (a) preparing an organic biostimulant composition comprising water and corn steep liquor; and (b) applying the organic biostimulant composition through a delivery system to a growth medium supporting plants. As used here, the term "cultivating" is broadly defined to refer to any number of activities, including fostering the growth of plants, preparing for growing plants, or any other means of promoting or improving the growth of a plant. In certain exemplary embodiments, the organic biostimulant composition is applied to a growth medium supporting plants that are crops. In certain exemplary embodiments, the organic biostimulant composition further comprises from one to five microbial strains as an inoculant. In certain exemplary and non-limiting embodiments, the method for cultivating plants further comprises applying supplemental liquid and water soluble fertilizer.

The application of the organic biostimulant composition is effective in producing economically valuable responses by targeted plants in a number of different ways. These responses may include, but are not limited to, increasing nutrient uptake, increasing plant yield, reducing susceptibility to disease, reducing disease damage, accelerating plant development, increasing harvestable material weight, or any combination of these. These and other economically valuable responses by the targeted plant will be recognized by those skilled in the art. In certain exemplary and non-limiting embodiments disclosed here, the biostimulant composition is effective in producing at least one economically valuable response when applied to a growth medium supporting a plant selected from the group consisting of increasing nutrient uptake, increasing plant yield, reducing susceptibility to disease, reducing disease damage, accelerating plant development, increasing harvestable material weight, or any combination of these. In certain exemplary and non-limiting embodiments disclosed here, the method of cultivating plants further comprises producing at least one economically valuable response as a consequence of applying the biostimulant composition to the growth medium.

In certain exemplary embodiments disclosed here, the biostimulant composition is effective in increasing plant yield by at least 5% as a consequence of applying the composition to a growth medium supporting plants. In certain exemplary embodiments disclosed here, the biostimulant is effective in increasing plant yield by at least 7%, at least 10%, at least 12%, at least 15%, at least 18%, or at least 20% as a consequence of applying the composition to a growth medium supporting plants. An increase in plant yield may exhibit itself in any one or more different ways, e.g., an increase in plant growth or size; an increase in biomass, i.e., an increase in produced biological material; an increase in harvestable material, e.g., fruits, vegetables, flowers, seeds, nuts, roots, fibers, or any other part of the plant which is of economic value; or any combination thereof. An increase in plant yield may also be exhibited by an increase in the yield stability of the plant, meaning that the yield is not strongly affected by changes in environmental conditions, such as adverse growing conditions caused by drought, chilling, flooding, freezing, heat, suboptimal pH, nutrient deficiency, or any combination of these.

It should be understood, that as used here, the phrase "growth medium supporting plants" or when the term "support" is used in reference to a growth medium, this should not be interpreted to refer to only the nutritional aspect of the plant health, and may instead refer to structural support or being capable of providing structural support.

In certain exemplary embodiments the biostimulant composition is applied to the growth medium supporting plants that are crops. As used here, the term "crop" refers to a plant or plant product that can be grown to be harvested as food, livestock fodder, fuel, or for any other economic purpose. Exemplary crops include e.g., high value crops, and staple crops. High value crops generally refer to non-staple agricultural crops, e.g., vegetables, fruits, flowers, ornamentals, condiments and spices. Most high value agricultural crops are those known to have a higher net return per hectare of land than staples or other widely grown crops. In certain exemplary embodiments the biostimulant composition is applied to growth medium supporting staple crops. In contrast to high value crops, staple crops are those that are common enough in diets around the world as to require significant quantities of land dedicated to growing them. A staple food is a food that can be stored for use throughout the year (or produced fresh any time of the year) and forms the basis of a traditional diet. Staple foods vary from region to region, but are typically inexpensive starchy foods of vegetable origin that are high in food energy (calories) and carbohydrates. Most staple foods derive either from cereals such as wheat, barley, rye, maize or rice, or starchy root vegetables such as potatoes, yams, taro, and cassaya. Exemplary staple foods also include pulses (dried legumes), sago (derived from the pith of the sago palm tree), and fruits such as breadfruit and plantains.

In certain exemplary embodiments the biostimulant composition is applied to the growth medium supporting plants selected from the group consisting of legumes, fruits, flowers, vegetables, or any combination thereof. In certain exemplary embodiments the biostimulant composition is applied to the growth medium supporting plants grown using plasticulture practices. In certain exemplary embodiments the biostimulant composition is applied to the growth medium supporting plants grown in beds or pots. Suitable plants for use with the biostimulant composition may include outdoor or indoor plants, and may be those grown in the home garden (both retail and individually grown).

In certain exemplary embodiments, the biostimulant composition is applied to growth medium supporting plants through a delivery system. The delivery system may take any one of a number of different forms. Non-limiting examples include pump driven or manually operated systems which may in turn be part of a larger irrigation system or apparatus. Such a system or apparatus may include one or more reservoirs, tubes and/or sprayers. Suitable irrigation systems may include, surface, e.g., flood; localized, e.g., drip, spray, micro-sprinkler, bubbler; sprinkler, e.g., center pivot, lateral move (side roll, wheel line), boom; sub-irrigation (seepage irrigation); or manual systems. Alternatively, the delivery system may take the form of a hydroponic system. Additional and alternative suitable delivery systems will be recognized by those skilled in the art given the benefit of this disclosure.

In certain exemplary embodiments, the biostimulant composition is applied to soil (e.g., field, potting) or other suitable growth medium. The growth medium may take any one of a number of different forms. Non-limiting examples include, peat and peat-like materials, e.g., hypnaceous moss, reed and sedge, humus, sphagnum moss; wood residues, e.g., sawdust, barks; bagasse; rice hulls; corn cobs; straw; peanut and pecan shells; sand; perlite; vermiculite; calcined clays; coir, soilless growing media, e.g., liquids, gels, hydroponic systems; or synthetic media, e.g., fiberglass, expanded polystyrene, urea formaldehyde.

In certain exemplary and non-limiting embodiments disclosed here, the biostimulant composition is applied to a growth medium that is deficient in nutrients and microbes. As used here, the term "deficient" means that there is an insufficient level or absence of a certain element or elements (e.g., nutrient or microorganism) beneficial to plant growth. Growth mediums that are deficient in nutrients and/or microbes will fail to provide the appropriate level of nourishment to the plants. In such a situation, the biostimulant composition will provide the nutrients necessary to feed airborne microbes, which will eventually populate the growth medium. In addition, the biostimulant composition may further comprise an inoculant that will provide the necessary microbes to ensure plant growth. These microbes may act alone or in cooperation with the airborne microbes. Liquid and water soluble fertilizer use may also be used in combination with such a system.

In certain exemplary and non-limiting embodiments disclosed here, the biostimulant composition is applied to a growth medium at a rate ranging from at least 0.006 oz per 1000 ft$^2$ to 6 oz per 1000 ft$^2$. Preferably the biostimulant composition is applied to a growth medium at a rate ranging from at least 1.5 oz per 1000 ft$^2$ to 6.0 oz per 1000 ft$^2$. More preferably the biostimulant composition is applied to a growth medium at a rate ranging from at least 2.0 oz per 1000 ft$^2$ to 6.0 oz per 1000 ft$^2$. The rate of application will depend on a number of factors, including the components of the biostimulant composition and their interaction with each other, the target plant species, what phase of the growth cycle the target plant is in, the climate and other external conditions, e.g., soil and moisture conditions, geography, and sun or shade conditions. Other factors affecting the rate of application will be recognized by those skilled in the art.

In certain exemplary and non-limiting embodiments disclosed here, the biostimulant compositions is applied to a growth medium at time intervals ranging from −5 days, up to every 35 days. The time interval between applications may be vary regularly (e.g., every 14 days) or it may be varied (14 day intervals; followed by a 7 day interval; followed by a 24 day interval; or the like). As used here, negative days (i.e., −5 days) indicate the number of days that precede planting. The time interval between applications will depend on a number of factors, including the components of the biostimulant composition and their interaction with each other, the target plant species, what phase of the growth cycle the target plant is in, the climate and other external conditions, e.g., soil and moisture conditions, geography, and sun or shade conditions. Other factors affecting the time interval between applications will be recognized by those skilled in the art.

Referenced here are trade names for components including various ingredients suitable for use in the exemplary products, compositions and methods disclosed here. The inventors do not intend to be limited by materials under a certain trade name. Equivalent materials (e.g., those obtained from a different source under a different name or reference number) to those referenced here by trade name may be substituted and utilized in the descriptions here.

It should be understood that biostimulant compositions in accordance with this disclosure may have any of numerous different specific formulations or constitutions. The formulation of a biostimulant composition in accordance with this disclosure can vary to a certain extent, depending upon such factors as the product's intended market segment, its desired characteristics, desired nutritional profile and the like.

EXAMPLES

In 2009 a field study experiment was performed in Pennsylvania to quantify the benefit of a biostimulant composition comprising 50 wt. % CSL in water both with and without two commercial microbial inoculant products using fresh market tomatoes as a test high value vegetable crop.

Example 1

Seeds of the tomato 'Mountain Fresh Plus' (Mountain Fresh Plus F1 Hybrid Variety, Developed by NC State University, Determinate, Nematode resistant, Disease Resistance: VFF, Gray Wall, Blossom End Rot, Puffiness, Angularity) were sown in a greenhouse on Apr. 17, 2009. Field planting was performed on Jun. 8, 2009 into black plastic mulch and the plants were staked and tied using the modified Florida weave trellis system.

A total of six replications with 6 treatments were used with a randomized complete block experimental design. Each experimental unit consisted of 24 plants in 36 ft plots. Each plot was about 32 inches wide, giving each treatment an area of about 96 ft$^2$, and each experimental unit an area of about 576 ft$^2$. There were 6 feet between rows. The randomization was carried out as shown below in Table 1:

TABLE 1

Field Randomization Scheme

|  | Treatment | Treatment | Treatment |
|---|---|---|---|
| Repetition 1 | 2 | 4 | 1 |
|  | 3 | 6 | 5 |
| Repetition 2 | 5 | 6 | 3 |
|  | 1 | 4 | 2 |
| Repetition 3 | 2 | 3 | 4 |
|  | 1 | 6 | 5 |
| Repetition 4 | 2 | 4 | 1 |
|  | 3 | 6 | 5 |
| Repetition 5 | 2 | 4 | 1 |
|  | 3 | 6 | 5 |
| Repetition 6 | 2 | 4 | 1 |
|  | 3 | 6 | 5 |

Table 2 describes each of the 6 different treatments. The "cocktail" microbial inoculant was applied at 46 oz per 1000 ft$^2$ and the "singular" microbial inoculant was applied at 2 oz per 1000 ft$^2$. The Daniels Biostimulant Additive was applied at 3 oz per 1000 ft$^2$. Water was used for the control.

TABLE 2

Treatment Descriptions

| No. | Name | Description |
|---|---|---|
| 1 | Control | No treatment |
| 2 | Cocktail | "Cocktail" microbial inoculant |
| 3 | Singular | "Singular" microbial inoculant |
| 4 | Corn Steep Liquor (CSL) Biostimulant Composition | Daniels Biostimulant Additive |
| 5 | Cocktail + CSL Biostimulant Composition | "Cocktail" microbial inoculant with Daniels Biostimulant Additive |
| 6 | Singular + CSL Biostimulant Composition | "Singular" microbial inoculant with Daniels Biostimulant Additive |

Tables 2A-2C disclose in greater detail treatments 2-4 listed above.

TABLE 2A

"Cocktail" Microbial Inoculant
Organica Biotech Plant Growth Activator (PGA) Plus
Component Description 52 species of beneficial soil bacteria, actinomycetes, and fungi
Amino Acids
Vitamins
Biotin
Folic acid
Natural Sugars

TABLE 2B

"Singular" Microbial Inoculant
Component Description

*Bacillus subtilis*

TABLE 2C

Daniels Biostimulant Additive

| wt % | Component Description |
|---|---|
| 50 | Corn Steep Liquor (CSL) |
| 50 | Water |

Field fertilization requirements were adjusted per the results of a separate soil test report. Additional fertilization was applied through fertigation with water soluble fertilizers (20-10-20, 300 ppm) at transplant and again two weeks later. Suckers were removed (per Pennsylvania Commercial Production Recommendations) to the first node below the first flower cluster on Jul. 7, 2009.

Table 3 lists the dates and details of each application:

TABLE 3

Application Details

| Date of Application | Details of Application |
|---|---|
| Jun. 6, 2009 | Performed with Dosatron injector and garden hose; Irrigated after application |
| Jul. 9, 2009 | Performed with Dosatron injector and garden hose; Irrigated after application |
| Jul. 28, 2009 | Performed with hand pump sprayer; Irrigated after application |
| Aug. 21, 2009 | Performed with hand pump sprayer; Irrigated after application |
| Sep. 18, 2009 | Performed with hand pump sprayer; Irrigated after application |

The ripening stages in the tomato fruit are described as immature, mature green, breaker, pink, and red. Mature greens have a white to yellow "star" on the blossom end, but the only definitive test of maturity is to cut the tomato in half. If the seeds are cut by the knife, the fruit is still immature. The breaker stage occurs within 24 hours of the mature green stage and is easily distinguished because the blossom end is pink. "Breakers" ripen naturally without gassing and are labeled in supermarkets as "vine-ripe." At the time of harvest, the entire field was harvested of all fruit at the breaker stage or any fruit exhibiting the more advanced stages of ripening. In total, there were 10 harvests before the first killing frost (occurring on Oct. 11, 2009). Fruit was harvested on the dates shown in Table 4 below:

TABLE 4

Harvesting Dates 2009

| August | 14, 19, 21, 24, 28 |
|---|---|
| September | 3, 13, 21, 28 |
| October | 7 |

At each harvest, the fruit were counted and subsequently graded into one of three categories, as described in Table 5 below:

TABLE 5

Categories for Harvested Fruit

| Grade | Description |
|---|---|
| 1 | Perfect fruit with no blemishes and of a standard size |
| 2 | Edible fruit, but with minor defects (i.e., blossom end scars, cracking or of a small size) |
| Culls | Unmarketable due to cracks, scars, rot, etc. |

Figure 2:
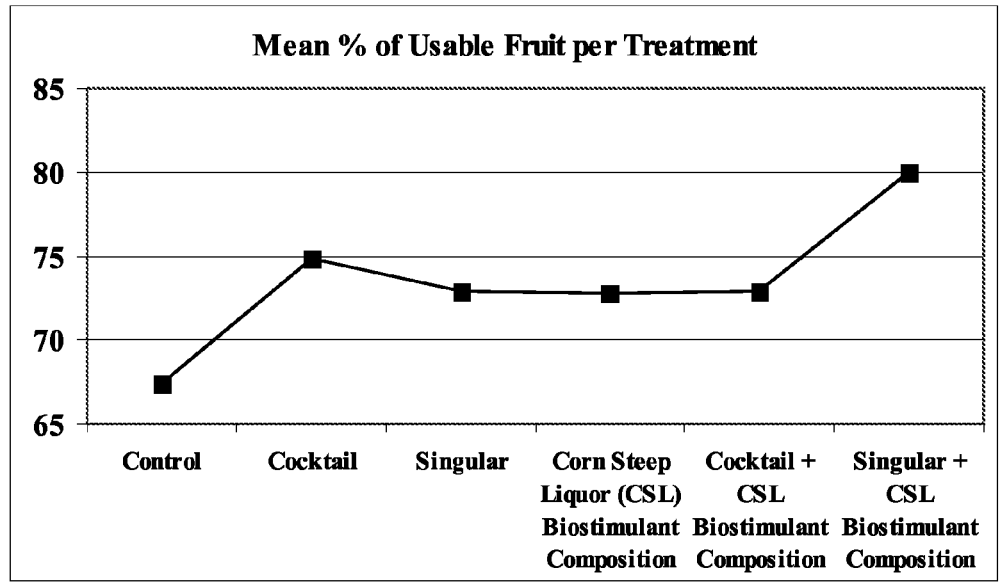
FIG. 2 illustrates the mean percent of usable fruit per treatment resulting from field testing performed on tomato plants.
Figure 3:
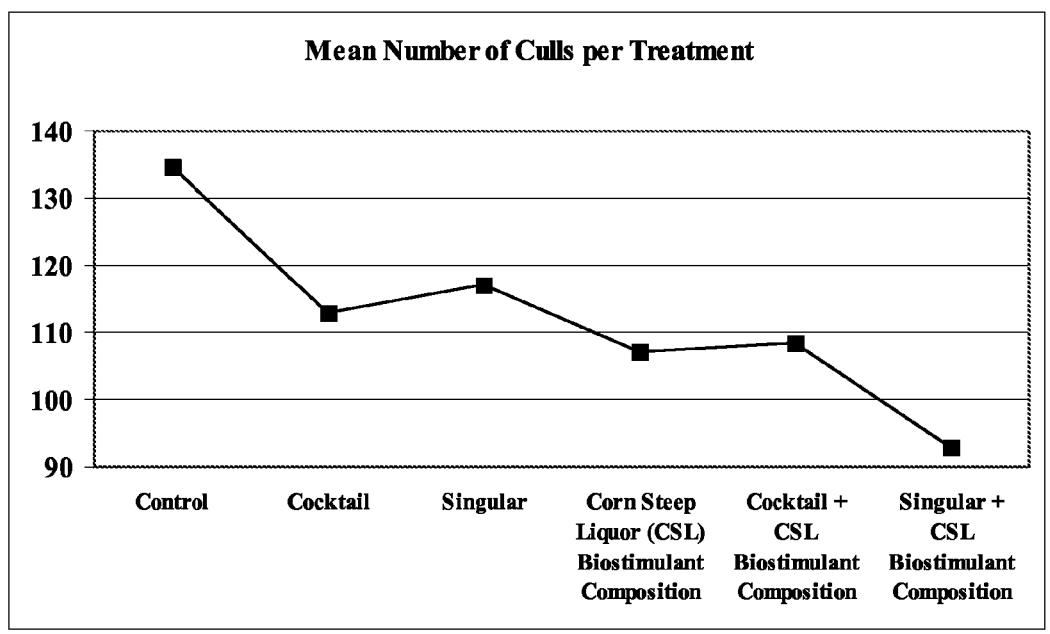
FIG. 3 illustrates the mean number of culls per treatment resulting from field testing performed on tomato plants.

For each of the three categories, the fruit weight was also measured at the time of harvest. Additional data was calculated and analyzed, including the percentages of Grade 1 and Grade 2 fruits, and the percentage of culls. Results are shown in the graphs of FIGS. 1, 2 and 3. The average total weight of fruit harvested per 36 ft plot over the course of the field test was 130 lbs, or about 5.4 lbs per plant. This number was considered to be of low yield and was attributed to the particular variety of tomato plant used in the study (Mountain Fresh Plus' is typically not a high yielding plant) and the abnormally poor growing conditions in the summer of 2009 (cold temperatures, low levels of sunlight and greater than normal amounts of rainfall). The first harvest (Aug. 14, 2009) also yielded a large number of culls. This was attributed to the fruit showing symptoms of late blight, and as a result, a phytophthora spray program was initiated in early August 2009 and continued as needed over the remainder of the growing season.

Despite unsatisfactory growing conditions, the data collected from the study (and shown in FIG. 1) showed two important trends: (1) The Daniels Biostimulant Additive, either alone or with inoculant was proven superior over traditional treatments and (2) the combination of the Daniels Biostimulant Additive with the "singular" microbial inoculant was proven superior over the "cocktail" microbial inoculant approach. Two specific results from FIG. 1 are plotted in FIGS. 2 and 3, which show the mean percent of usable fruit per treatment and the number of culls per treatment respectively.

The Daniels Biostimulant Additive comprising CSL was proven superior over the first control (which received no biostimulant or inoculant), yielding over 10% more usable fruit with greater weight and better quality. Additionally, combining the Daniels Biostimulant Additive with either form of microbial inoculant ("cocktail" or "singular") outperformed both of the treatments using only the microbial inoculant, yielding a higher mean number of usable fruit of greater quality. Furthermore, combining the Daniels Biostimulant Additive with the "singular" microbial inoculant was found to outperform the combination with the "cocktail" microbial inoculant in terms of the percentages and weight of usable fruit harvested in the study.

It should be understood that the word "about" is used herein to account for variance in measurements due to inherent errors associated with measurement techniques. The word "about", even if not explicitly used, is understood to modify all measurements disclosed, unless otherwise stated.

It should likewise be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended and, so, does not exclude additional items, features, components, etc.

Finally, although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the inventive systems, methods and devices defined by the following claims.

Given the benefit of the above disclosure and description of exemplary embodiments, it will be apparent to those skilled in the art that numerous alternative and different embodiments are possible in keeping with the general principles of the invention disclosed here. Those skilled in the art will recognize that all such various modifications and alternative embodiments are within the true scope and spirit of the invention. The appended claims are intended to cover all such modifications and alternative embodiments.

What is claimed is:

1. An aqueous organic biostimulant composition consisting of water, oilseed extract, *Bacillus subtillis*, and corn steep liquor; and
   wherein the concentration of the corn steep liquor in the aqueous composition is between about 0.10% and about 100% by weight;
   with optional additives in the composition selected from one or more of:
   (a) a supplement selected from the group consisting of natural glycerol, humate, fulvate, acetic acid, propionic acid, citric acid, lactic acid, or combinations thereof; and
   (b) from one to five additional microbial strains as an inoculant; and
   wherein the aqueous organic biostimulant composition when applied to a growth medium is effective in enhancing the growth of indigenous microorganisms present in the growth medium.

2. The aqueous organic biostimulant composition of claim 1, wherein the concentration of the corn steep liquor is between about 0.10% and 10% by weight, with the remainder of the composition consisting of water.

3. The aqueous organic biostimulant composition of claim 1, wherein the concentration of the corn steep liquor is between about 10% and 90% by weight, with the remainder of the composition consisting of water.

4. The aqueous organic biostimulant composition of claim 1, wherein the concentration of the corn steep liquor is between about 20% and 80% by weight, with the remainder of the composition consisting of water.

5. The aqueous organic biostimulant composition of claim 1, wherein the concentration of the corn steep liquor is between about 40% and 60% by weight, with the remainder of the composition consisting of water.

6. The aqueous organic biostimulant composition of claim 1, further including a supplement selected from the group consisting of natural glycerol, humate, fulvate, acetic acid, propionic acid, citric acid, lactic acid, or combinations thereof.

7. The aqueous organic biostimulant composition of claim 1, further including from one to five microbial strains as an inoculant; and wherein the concentration of the corn steep liquor is between about 0.10% and about 100% by weight.

8. The organic biostimulant composition of claim 7, wherein the number of additional microbial strains in the inoculant is from one to three.

9. The organic biostimulant composition of claim 7, further including a supplement selected from the group consisting of natural glycerol, humate, fulvate, acetic acid, propionic acid, citric acid, lactic acid, or combinations thereof.

10. The organic biostimulant composition of claim 7, wherein the organic biostimulant is effective in enhancing the growth of indigenous microorganisms in a growth medium and the one to five microbial strains in the inoculant.

11. A method of cultivating plants, comprising the steps of:
    preparing an organic biostimulant composition consisting essentially of water, corn steep liquor, oilseed extract, and *Bacillus subtillis*; and
    applying the organic biostimulant composition through a delivery system to a growth medium supporting plants.

12. The method of cultivating plants of claim 11, wherein the concentration of the corn steep liquor in the organic biostimulant composition is between about 0.10% and 100% by weight.

13. The method of cultivating plants of claim 11, wherein the organic biostimulant composition further includes a supplement selected from the group consisting of natural glycerol, humate, fulvate, acetic acid, propionic acid, citric acid, lactic acid, or combinations thereof.

14. The method of cultivating plants of claim 11, wherein the organic biostimulant enhances the growth of indigenous microorganisms in the growth medium.

15. The method of cultivating plants of claim 11, wherein the organic biostimulant composition further includes from one to five microbial strains as an inoculant.

16. The method of cultivating plants of claim 15, further including producing at least one economically valuable response as a consequence of applying the biostimulant composition to the growth medium.

17. The method of cultivating plants of claim 16, wherein the organic biostimulant enhances the growth of indigenous microorganisms in the growth medium and the one to five microbial strains in the inoculant.

* * * * *